(12) United States Patent
Mironov et al.

(10) Patent No.: US 11,427,802 B2
(45) Date of Patent: Aug. 30, 2022

(54) METHOD AND APPARATUS FOR PRINTING BIOLOGICAL TISSUES AND ORGANS

(71) Applicant: Private Institution Lab For Biotechnological Research "3D Bioprinting Solutions", Moscow (RU)

(72) Inventors: Vladimir Alexandrovich Mironov, Moscow (RU); Yusef Dzhordzhevich Khesuani, Moscow (RU); Alexandr Nikolaevich Mitryashkin, Moscow (RU); Irina Sergeevna Gladkaya, Moscow (RU); Alexandr Yurievich Ostrovsky, Moscow (RU); Sergei Vladimirovich Novoselov, Puschino Moskovskaya obl. (RU)

(73) Assignee: PRIVATE INSTITUTION LABORATORY FOR BIOTECHNOLOGICAL RESEARCH "3D BIOPRINTING SOLUTIONS", Moscow (RU)

(*) Notice: Subject to any disclaimer, the term of this patent is extended or adjusted under 35 U.S.C. 154(b) by 416 days.

(21) Appl. No.: 16/665,187

(22) Filed: Oct. 28, 2019

(65) Prior Publication Data
US 2020/0056147 A1 Feb. 20, 2020

Related U.S. Application Data

(62) Division of application No. 15/311,242, filed as application No. PCT/RU2015/000505 on Aug. 12, 2015.

(30) Foreign Application Priority Data

Sep. 5, 2014 (EA) .................................. 201401046

(51) Int. Cl.
*B33Y 10/00* (2015.01)
*C12N 5/00* (2006.01)
(Continued)

(52) U.S. Cl.
CPC ............ *C12N 5/0062* (2013.01); *B33Y 10/00* (2014.12); *B33Y 30/00* (2014.12); *B33Y 70/00* (2014.12);
(Continued)

(58) Field of Classification Search
None
See application file for complete search history.

(56) References Cited

U.S. PATENT DOCUMENTS 5,134,569 A * 7/1992 Masters ................ B29C 64/106
425/162
8,639,484 B2 1/2014 Sun et al.
(Continued)

OTHER PUBLICATIONS

International Search Report issued in PCT/RU2015/000505 dated Dec. 24, 2015 (w/ translation).
(Continued)

*Primary Examiner* — Mohammad M Ameen
(74) *Attorney, Agent, or Firm* — Nixon & Vanderhye PC

(57) ABSTRACT

The invention relates to medicine and biology, particularly to the means for artificial manufacturing of biological tissues and organs, and can be used in biotechnology, bioengineering, tissue engineering, regenerative medicine, and in the 3D-printing of biological tissues and organs.
Technical character of the invention consists in the development of a method of printing living tissues and organs as well as of the apparatus for its implementation. The proposed apparatus consists of at least:
a printing platform,
a bioink printing module with at least one nozzle designed for bioink dosing,
(Continued)

a gel-forming composition printing module, containing a UV-module, and at least one nozzle capable of dosing gel-forming composition that starts polymerizing under the influence of UV radiation, и a module for relatively displacing the nozzles and/or the platform, and in which the bioink printing module is separated from the gel-forming-composition printing module in such a way so as to prevent UV radiation from reaching the bioink printing module, the radiation from the UV module being directed predominantly parallel to the platform for printing, in such a way so as to prevent UV radiation from reaching the biological tissues and/or organs being printed.

The technical result of the invention is the development of a multi-functional device capable of combining various printing modes, providing a method of high-resolution printing of living tissues and organs based on UV-induced hydrogel polymerization, and a method of cell protection from UV radiation during the printing process.

8 Claims, 5 Drawing Sheets

(51) Int. Cl.
| | | |
|---|---|---|
| B33Y 80/00 | (2015.01) | |
| B33Y 70/00 | (2020.01) | |
| B33Y 30/00 | (2015.01) | |
| C12M 1/26 | (2006.01) | |
| C12M 3/00 | (2006.01) | |

(52) U.S. Cl.
CPC ............ *B33Y 80/00* (2014.12); *C12M 21/08* (2013.01); *C12M 33/00* (2013.01); *C2N 5/00* (2013.01); *C12N 2533/50* (2013.01); *C12N 2533/52* (2013.01); *C12N 2533/74* (2013.01)

(56) References Cited

U.S. PATENT DOCUMENTS

| | | |
|---|---|---|
| 2003/0025086 A1 | 2/2003 | Stroka |
| 2006/0118198 A1 | 6/2006 | Eisenhut |
| 2008/0089731 A1 | 4/2008 | Szoke |
| 2009/0239302 A1 | 9/2009 | Decher et al. |
| 2009/0263849 A1* | 10/2009 | Sun ................... B01L 3/502707 435/29 |
| 2010/0249044 A1* | 9/2010 | Walker .................. A61L 24/06 435/404 |
| 2011/0212501 A1* | 9/2011 | Yoo ........................ C12M 25/14 427/337 |
| 2011/0280914 A1* | 11/2011 | Prestwich ............... B22F 1/102 977/773 |
| 2012/0089238 A1 | 4/2012 | Kang et al. |
| 2014/0093932 A1* | 4/2014 | Murphy ................. B33Y 30/00 435/177 |

OTHER PUBLICATIONS

Abstract of Fleming et al., "Fusion of uniluminal vascular spheroids: a model for assembly of blood vessels" *Developmental Dynamics*, vol. 239, No. 2: 398-406 (Feb. 2010).

Abstract of Gentile et al., "VEGF-mediated fusion in the generation of uniluminal vascular spheroids" *Developmental Dynamics*, vol. 237, No. 10: 2918-2925 (Oct. 2008).

Abstract of Visconti et al., "Towards organ printing: engineering an intra-organ branched vascular tree" *Expert Opinion on Biological Theroy*, vol. 10, No. 3: 409-420 (Mar. 2010).

Dragon (I ddragon). Bioprinter uzhe realnost, Feb. 26, 2010, p. 1-5, 1-25 rip. 1-6. Found on the Internet: i-ddragon livjournal.com-41263.html).

* cited by examiner

METHOD AND APPARATUS FOR PRINTING BIOLOGICAL TISSUES AND ORGANS

This application is a divisional of U.S. application Ser. No. 15/311,242 filed on Nov. 16, 2016, which is the U.S. national phase of International Application No. PCT/RU2015/000505 filed on Aug. 12, 2015, which designated the U.S. and claims the befit of EA 201401046 filed on Sep. 5, 2014, the entire contents of each of which are hereby incorporated herein by reference.

The invention relates to medicine and biology, particularly to the means for artificial manufacturing of biological tissues and organs, and can be used in biotechnology, bioengineering, tissue engineering, regenerative medicine, and in the 3-D printing of biological tissues and organs.

BACKGROUND TECHNOLOGY

The "Method and apparatus for computer-aided tissue engineering for modeling, design and freeform fabrication of tissue scaffolds, constructs, and devices", U.S. Pat. No. 8,639,484 B2, published 28 Jan. 2014, IPC G06G7/48, B29C67/00, A01N63/00, B29C41/00, B29C41/52, G06F17/50), describes the process and apparatus for manufacturing complex parts and devices using a CAD model and multi-nozzle biopolymer deposition apparatus for 3D printing of biological tissues and organs. One main disadvantage of this technology is a low-level printing resolution.

Another solution is described in the US Patent Application "Integrated organ and tissue printing methods, system and apparatus", US20120089238A1, published 12 Apr. 2012, IPC A61F2/02, B05D1/00, B05C11/00), provides the method and apparatus for organs and organ constructs using a structural support polymer and a live cell-containing composition. One main disadvantage of this technology is a low-level printing resolution.

The solution described in US Patent Application "Method for constructing functional living materials, resulting materials and uses thereof", US20090239302A1, published 24 Sep. 2009, IPC C12N5/06), concerns a method for constructing a functional living biomaterial by assembling layer by layer a matrix of functional living cells. One main disadvantage of this technology is a low-level printing resolution, i.e. insufficient reproduction accuracy of CAD model form.

Chosen as a prototype is the solution described in US Patent Application "Devices, systems, and methods for the fabrication of tissue utilizing UV cross-linking", US20140093932A1, published 3 Apr. 2014, IPC C12M1/00, C12M3/00, C12N5/00), concerning bioprinters comprising one or more printer heads for bioink and support material, a UV light module to initiate polymerization, as well as the methods of using such bioprinters. One main disadvantage of this technology is cell exposure to UV radiation during printing which causes damage to live cells.

Objective Technical Problem

Technical problem of the invention is to provide printing of live functional biological tissues and organs in high resolution, i.e. precise 3D positioning in accordance with the CAD model of tissue spheroids with high density, as well as to provide cell protection from UV radiation while printing biological tissues and/or organs on the basis of hydrogel materials.

Technical result includes solution of the technical problem and development of the multi-functional device capable of combining various printing modes

Solution

To solve this problem we propose the following solution group (apparatus and methods). Apparatus for printing of biological tissues and organs, comprising at least
a printing platform,
a bioink printing module with at least one nozzle designed for bioink dosing,
a gel-forming-composition printing module, containing a UV-module, and at least one nozzle capable of dosing a gel-forming composition that starts polymerizing under the influence of UV radiation, и
a module for relatively displacing the nozzles and/or the platform,
and in which the bioink printing module is separated from the gel-forming-composition printing module in such a way so as to prevent UV radiation from reaching the bioink printing module, the radiation from the UV module being directed predominantly parallel to the platform for printing, in such a way so as to prevent UV radiation from reaching the biological tissues and/or organs being printed.

The apparatus can be designed so as to achieve separation of the bioink printing module from the gel-forming composition printing module either by providing sufficient spacing between the above-mentioned modules or by providing a barrier protecting the bioink printing module from being exposed to UV radiation.

The apparatus can be designed so as to implement the gel-forming composition module with the nozzles designed for deposition of the printing material.

The apparatus can be designed so as to implement a UV module whereby the height of the UV light emitting source can be controlled relative to the platform and the intensity of UV radiation emitted by the light source can be controlled as well.

The apparatus can be designed so as to implement a protection module designed to pick up UV radiation not absorbed by the gel-forming composition.

The apparatus can be designed so as to implement a hollow-section protection module coated from inside with a UV-absorbing material.

The apparatus can be designed so as to implement the displacing module comprising a laser system for nozzle positioning with the accuracy up to 5 μm.

The apparatus can be designed so as to use tissue spheroids and/or gel-forming composition with living cells as bioink.

The apparatus can be designed so as to use a gel0forming composition which is a controlled alginate gel-forming system containing liposomes with calcium ions bound in it, and released from the liposome matrix upon exposure to UV light.

The apparatus can be designed so as to implement nozzles with the diameter between 80 μm and 2.108 μm.

The apparatus can be designed so as to implement at least two separate units:
a. the printing unit comprising at least one bioink printing module, one gel-forming composition printing module, one module for displacing the nozzles relative to the platform and
b. the control unit comprising at least a printing unit control system and an operator panel for data input.

The apparatus can be designed so as to use wireless data link between the control unit and the printing unit.

The apparatus can be designed so as to implement a plastic semitransparent enclosure to protect from dirt the internal elements of the apparatus, including nozzles.

The apparatus can be designed so as to implement a gel-forming composition printing module comprising two nozzles and a bioink printing module comprising three nozzles.

The apparatus can be designed so as to implement a compressor connected to the nozzles to provide printing pressure between 4.8 bar and 6.2 bar.

The proposed apparatus can implement a layer by layer method of biological tissue and organ printing using bioink or a gel-forming composition polymerizing when exposed to UV light and involving the following stages of each individual layer forming:

a. acquiring data on the object's layer selected for printing;
b. deposing on the final surface a gel-forming composition polymerizing when exposed to UV light and which in the process of the deposition, i.e. after being released from the nozzle and before deposition of the biological tissue or organ being printed, is exposed to UV radiation;
the bioink printing module is separated from the gel-forming-composition printing module in such a way so as to prevent UV radiation from reaching the bioink printing module, the radiation from the UV module being directed predominantly parallel to the platform for printing, in such a way so as to prevent UV radiation from reaching the biological tissues and/or organs being printed, and the amount of gel-forming composition is calculated so as to form the required hydrogel layer upon completion of the polymerization process;
c. applying bioink on the layer formed with the gel-forming composition at the previous stage (b) in accordance with the data acquired at stage (a);
d. wait on hydrogel polymerization completion.

Implementation of the method can involve spheroids used as the bioink.

The method whereby the ratio between the spheroid diameter and the thickness of the polymerized hydrogel layer is selected so that the thickness of the latter will be less than the spheroid diameter.

The method whereby the spheroid diameter cab be selected in the range between 100 µm and 2.108 mm, and the polymerized hydrogel layer thickness in the range between 80 µm and 0.6414 mm.

The method whereby the polymerization time is in the range between 5 s and 5 min.

The method whereby a gel-forming composition is a controlled alginate gel-forming system containing liposomes with calcium ions bound in it, and released from the liposome matrix upon exposure to UV light.

The method whereby at least one layer is printed with the use of bioink and at least two substances capable of polymerization when contacting each other, including the following stages:

a. acquiring data on the object's layer selected for printing;
b. deposing the substances on the final surface so as to obtain the required hydrogel layer after the polymerization process is completed;
c. applying bioink onto the layer formed with the gel-forming composition at the previous stage (b) in accordance with the data acquired at stage (a);
d. wait on hydrogel polymerization completion.

The method whereby fibrinogen and thrombin are used as the substances polymerizing upon getting in contact with each other.

The method whereby alginate and calcium ions are used as the substances polymerizing upon getting in contact with each other.

The method whereby at least one layer is printed using live-cell hydrogel as bioink.

Definition of the terms used in the patent application materials is given below.

Bioprinter—a device for printing biological tissues and organs.

Bioink—printing material used in a bioprinter to allow for the formation of biological tissues and organs. For example, bioink materials can include cells, hydrogel with cells or complex systems—spheroids (tissue spheroids) represented by groups of cells forming spherical structures as a result of a contact with each other. Spheroids can be protected by a temporary spherical enclosure (consisting for example of hydrogel) preventing tissue spheroids from merging with each other.

Gel-forming composition (biopaper)—printing biomaterial used for fabrication of a tissue or organ scaffold. The basic property of gel-forming compositions in this invention is the ability for polymerization and transformation from the living state allowing free deposition of bioink into a hydrogel to provide scaffold supporting bioink during the time required for the formation of the organ or tissue. Different mechanisms can be used to initiate polymerization for hydrogel formation, for example, light initiated polymerization, including that by UV light, chemically initiated polymerization. In one option gel-forming composition is represented by a controlled alginate gel-forming system consisting of alginate and liposomes degrading when exposed to UV radiation and releasing calcium ions bound in them. Calcium ions released from liposomes form ionic linkages with the negatively charged group of G residue from two different alginate polymers which results in cross-linking of both polymers. Alginate polymer cross-linking results in the formation of the matrix forming the structure of the alginate gel layer. Fibrinogen and thrombin is one more example of a gel-forming composition whereby thrombin contacts with fibrinogen to initiate polymerization of the latter and formation of fibrin.

For the purposes of this invention, hydrogel produced from gel-forming composition shall be biologically compatible with the cells, be non-toxic, cause minimum immune response, and be promotive for cell proliferation without causing damage to them. Also, hydrogel shall be biodegradable.

It should be noted that different gel0forming compositions with different polymerization mechanism can be used. Among them are gel-forming compositions with light initiated polymerization, or with polymerization initiated by ions, temperature and acidic Ph value, or by other factors. Listed in Table 1 are some gel-forming compositions with different polymerization mechanisms that can be used for printing.

TABLE 1

| Polymer | Varieties | Polymerization method |
|---|---|---|
| Synthetic | | |
| Полиэтиленгликоль (ПЭГ) Polyethyleneglycol (PEG) | Полиэтиленгликоль - диакрилат (ПЭГДА) PEG-diacrylate (PEGDA) | Light-initiated |
| | ПЭГдиметакрилат (ПЭГДМА) PEGdimethacrylate (PEGDMA) | Light-initiated |
| МультицепочечныйПЭГ MultiarmPEG (maPEG) | ПЭГпептид PEG peptide | Photosensitive |
| | ПЭГ - акрилат maPEG acrylate | Photosensitive; chemical (Michael reaction) |
| | ПЭГ - азид maPEGazide | Chemical |
| | ПЭГ - тиол maPEGthiol | Chemical (Michael reaction) |
| Полиакриламид Poly(acrylamide) (PAm) | | Photosensitive |
| Полиизопропилакриламид Poly(N-isopropyl acrylamide) (PNIPAAm) | | Photosensitive |
| Полигидроксиэтилметакрилат Poly(2-hydroxyethyl methacrylate) (PHEMA | | Photosensitive |
| Natural | | |
| Agarose | | Thermal |
| Alginate | | Ion-sensitive, calcium |
| Collagen | | Thermal, pH |
| Fibrin | | Chemical (Fibrinogen + thrombin) |
| Gelatin | | Thermal, pH |
| | Желатинаметакрилат Gelatin methacrylate (GelMA) | Photosensitive |
| Hyaluronic acid | | Chemical, cross-linking agent not required |
| | Метакрилат / акрилат гиалуроновой кислоты Methacrylate/acrylatehyaluronicacid (MeHA/AHA) | Photosensitive |
| Матригель (Matrigel) | | Thermal |

By the term "cells" this description implies the cells of biological tissue and/or organs.

Resolution—the number of cells per volume unit characterizing the accuracy of the digital model replication using bioink and gel-forming composition for printing with a bioprinter. The higher the resolution, the more accurately the organ or biological tissue can be replicated.

DRAWING DESCRIPTION

INDICATIONS USED ON THE DRAWINGS

1—Bioink printing nozzle,
2—X-Y axes positioning system (module for nozzle positioning relative to the platform),
3—L-shaped supporting structure for fixing the nozzles and the positioning system on Z axis,
4—Printing unit,
5—Nozzle for gel-forming composition printing,
6—Gel-forming composition,
7—UV radiation absorption unit,
8—Supporting structure,
9—UV radiation source,
10—Exposure of gel-forming composition to UV radiation,
11—Petri cup, 12—Polymerizable material layer,
13—Digital video camera (camera) for printing process supervision,
14—Printing calibration system,
15—Biological tissue and organs holder,
16—System for control of air feed to printing nozzles,
17—Nozzle control system for polymerizable materials,
18—UV emitter control system,
19—Spheroid.

DETAILED DESCRIPTION OF THE SOLUTION

To protect cells against ultraviolet (UV) radiation in the process of printing biological tissue and/or organ based on the polymerizable material and for high printing resolution to provide precise spatial positioning and holding of the set high-density tissue spheroid model, it is suggested to apply the following device and methods.

Figure 1:
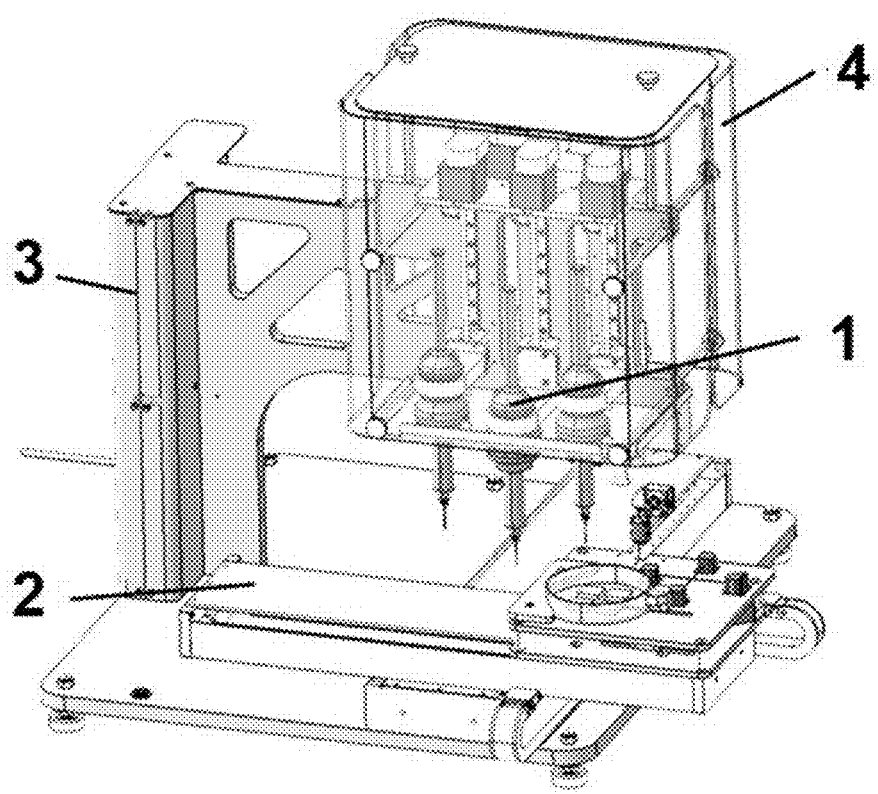
FIG. 1 shows the appearance of the bioprinter.
Figure 2:
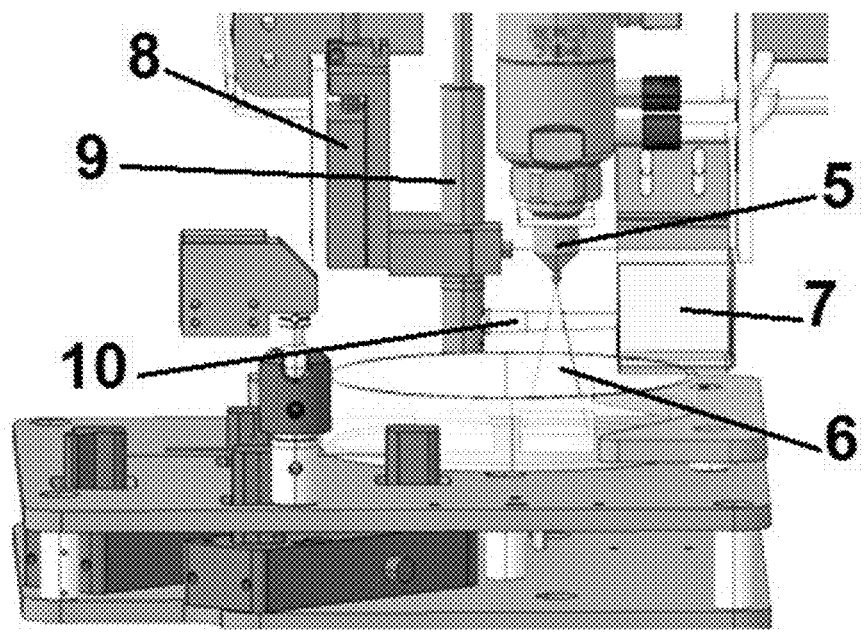
FIG. 2 shows the process of polymerizable material spraying with simultaneous exposure to UV-radiation for triggering the polymerization process without cell damage.
Figure 3:
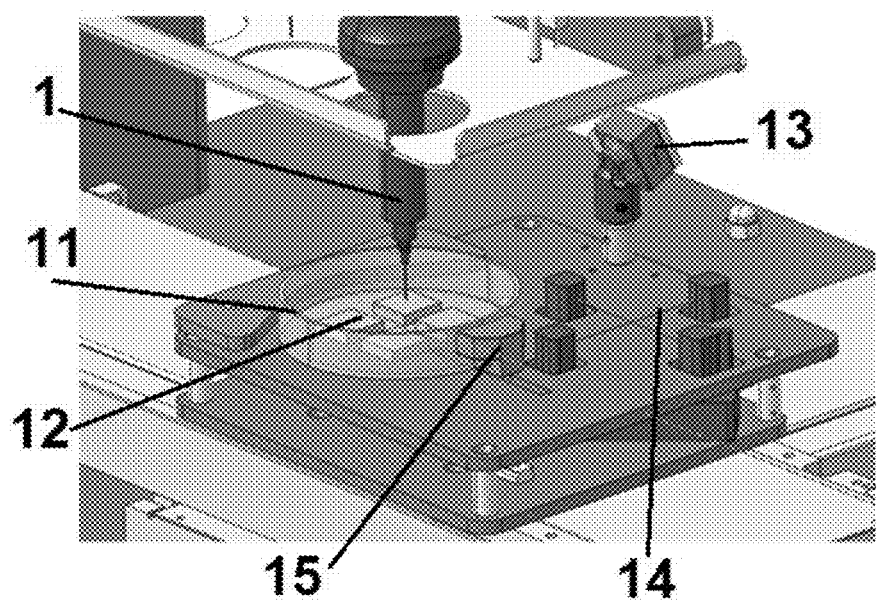
FIG. 3 shows the three-dimensional system of positioning and calibration.
Figure 4:
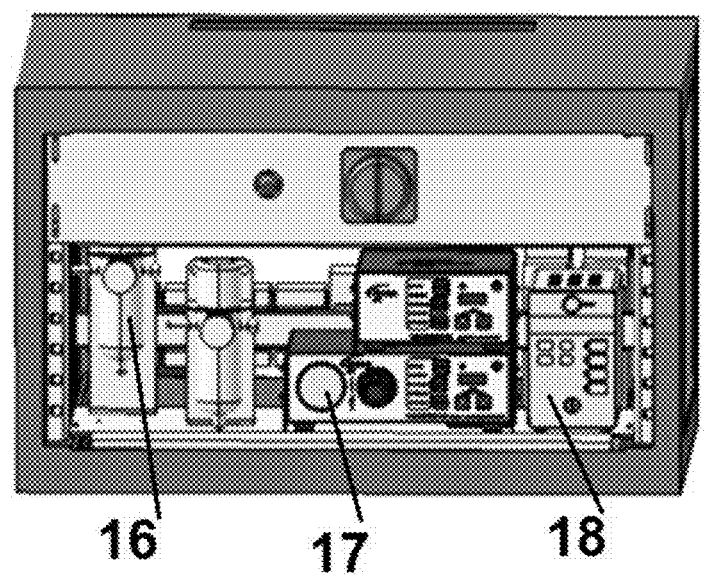
FIG. 4 shows the bioprinting control system.

The developed apparatus—bioprinter for printing biological tissue and organs consists of:
printing platform;
bioink printing unit (4) with three nozzles (1) with the function of bioink dosing which allows, e.g., simultaneous printing at different resolution settings with three various types of tissue spheroids of different diameter and structure (solid—a combination of cells only or cells and spherical hydrogel, luminal—the same combination, but of a bagel-like shape with a hole inside it, concentric or encapsulated—with one spheroid located inside the other one, janus-like or composite—a peripheral spheroid consisting of one type of cells and the one in the center consisting of different cell types (for detailed information about spheroids refer to the articles "Towards organ printing: engineering an intra-organ branched vascular tree" by Visconti R P, Kasyanov V, Gentile C, Zhang J, Markwald R R, Mironov V., published in 2010, "VEGF-mediated fusion in the generation of uniluminal vascular spheroids" by Gentile C, Fleming P A, Mironov V, Argraves K M, Argraves W S, Drake C J., published in 2008, "Fusion of uniluminal vascular spheroids: a model for assembly of blood vessels" by Fleming P A, Argraves W S, Gentile C, Neagu A, Forgacs G, Drake C J., published in 2010);
gel-forming composition printing unit with two nozzles (5), which can use for printing either UV-radiation polymerizable gel-forming composition or materials that polymerize when contacting each other, UV radiation source (9) with supporting structure (8) that enables adjustment of UV emitter elevation and UV radiation absorption unit (7) to prevent exposure of biological tissue, organs and cells to UV radiation;
positioning system (a module for relatively displacing of nozzles and platform) in the proposed version serving for movement of the platform for printing of biological tissue or organ (15) along axes X-Y (2), while the nozzles are moved along Z axis;
L-shaped supporting structure for fixing the nozzles and the positioning system on Z axis (3) that provides more room for nozzle placement and optimal access to tissue construct;
printing calibration system (14);
digital camera for supervision of the printing process (13);
printing control system (FIG. 4), in its turn consisting of the system for control of air feed to printing nozzles (16), system for control of nozzles for polymerizable materials (17), UV emitter control system (18) and system for control of the positioning system' stepping motors;
special-purpose CAD/CAM software designed for modeling and/or import of digital models for printing and printing process control.

The printer provides for UV radiation exposure of gel-forming composition at the moment of its spraying which allows extension of the polymerization process and ensures e.g. smooth placement of tissue spheroids layer in the dispersed layer of gel-forming composition. In addition, to avoid exposure of bioink, biological tissue, organs and cells to diffuse UV radiation, a protection unit is used for picking up the non-absorbed UV radiation, while the direction of UV radiation from the unit which can be designed as a light emitting source should be mostly perpendicular to the direction of the material output from the respective nozzle and parallel to the surface of platform with the biological tissue and/or organ, in order to avoid direct UV exposure of cells, biological tissue and/or organs. The UV protection unit can be designed as a hollow-section module coated from inside with a UV-absorbing material.

The UV protection unit design provides for capability of gel-forming composition spraying to create a homogeneous polymerizable layer that serves for spatial placement, fixture and position stabilization of tissue spheroids. In this case the gel-forming composition is first dispersed, and then spheroids are built in the produced layer in compliance with the digital model.

Alginate containing liposomes with calcium ions can be used as gel-forming composition. The UV radiation source initiates polymerization through disruption of liposome membranes and release of calcium ions.

Five nozzles three of which use bioink while the other two print with gel-forming composition allow simultaneous application of various materials including but not limited to the following: cells, cell-containing gel-forming compositions, spheroids.

Within the proposed method different mechanisms can be used for polymerization initiation, e.g. photochemical polymerization including UV radiation exposure or chemical initiation of polymerization. This multi-functionality shall be achieved through application of the second nozzle for hydrogel printing. I.e. 5 nozzles and UV emission source shall enable implementation of various mechanisms using different hydrogels for fixing and stabilization of tissue spheroids in the model.

The movement unit (a system for precise laser positioning system for nozzles, with automatic calibration) enables the movement of nozzles with the accuracy up to 5 μm, therefore e.g. adjacent spheroids can be placed in direct contact with each other thus supporting high print quality. The printing process can be monitored in a real-time mode by a digital video camera installed near to the nozzles. Accurate positioning of nozzles ensures high compliance of the printed biological construct with the set digital model.

The printing process is controlled by the software that allows using different number of nozzles in a variety of combinations as well as to handle file formats for polygonal modeling. The software is compatible with various 3D modeling software complexes.

The designed apparatus includes bioink printing nozzles with the cone size ranging from 100 μm to 2.108 mm, while gel-forming composition printing nozzle cones range in size from 80 μm to 0.6414 mm. During the printing process the pressure in nozzles reaches 4.8-6.2 bar. Both nozzles for applying bioink and nozzles for applying gel-forming composition can be mounted on the supporting structure. Bio-printing control system (FIG. 4) is configured to match the number and type of installed nozzles. Elevation of UV source can be regulated with the help of supporting structure (8), and such parameters as UV emission duration and radiation source operating mode can be regulated with the help of controller (18). Printing parameters for nozzles are regulated with the help of control units 16 and 17. Printing control system allows quick switching between different printing modes. Printing convenience and accuracy are provided by automatic calibration and tuning at mode switching. The apparatus can be designed so as to implement at least two separate units: (a) printing unit at least including nozzles, UV radiation unit, moving platform (b) control unit at least including a printing unit control system, a system for input of data by the operator. This design of the system allows maximal reduction of the printing unit size and, moreover, provides the required level of sterility during cell handling and protection against pollution. Information between the control unit and printing unit can be transferred by wireless methods. The apparatus can be designed so as to implement a plastic semitransparent enclosure to protect the internal components, including the nozzles, from dirt and to provide sterility of the printing process.

Figure 5:
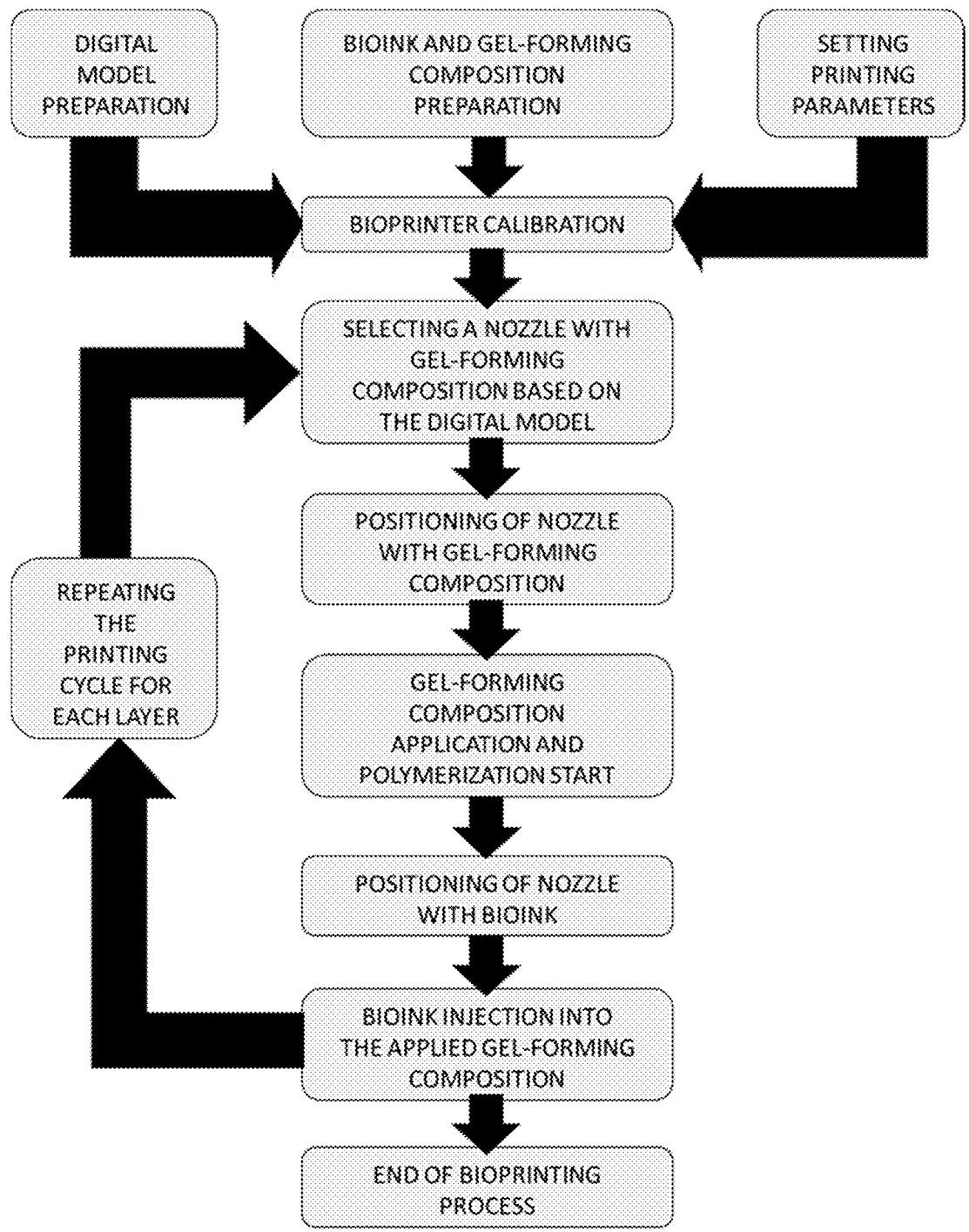
FIG. 5 shows the structure of the printing algorithm.

The printing process includes the following stages: preparation of a model, bioink to be printed and gel-forming composition, setting printing parameters, bioprinter calibration, and printing process itself. Block diagram of the complete printing process is shown on FIG. 5. The prepared model is uploaded to CAD/CAM—a specialized software for printing control. The digital model can be prepared by using this software itself or imported from some other application capable of three-dimensional modeling. Preparation of bioink (if spheroids are used) consists in the formation of homogeneous spheroids of certain size and in sufficient amount. Spheroid sizes range from 100 μm to 2.108 mm, while the polymerizable layer thickness ranges from 80 μm to 0.6414 mm. Usually the selected size of spheroids is bigger than the polymerizing hydrogel layer thickness which shall ensure good contact between spheroids in different layers.

The printing setting parameters: the distance between the printing nozzles in X-Y-Z positions, the dosed (dispersed) volume of bioink, gel-forming composition application parameters, duration and intensity of the UV emission source operation. Bioprinter calibration is performed with the help of a precision positioning system with a tolerance of 5 μm. Bioprinter calibration is performed once in the beginning of printing process.

Bioprinting process is cyclically repeated following the program based on the digital model. First, a nozzle that will apply bioink is selected, then the nozzle with a gel-forming composition is positioned, and then the latter is applied into a Petri cup (11) locked in a holder (15). During application the gel-forming composition (6) is exposed to UV radiation with the wavelength of 365 nm (10), or is mixed with other components initiating the polymerization process which can last from 5 s to 5 min. Then the bioink printing nozzles are positioned, and the bioink is placed in the dispersed layer of polymerizable hydrogel (12). The cycle is repeated (FIG. 5) with new coordinates in accordance with the digital model until the whole model is printed. Notably, this includes both printing with a basic gel-forming composition containing cells and various combinations and sequences of printing. Printing process can be continuously monitored online by a digital video camera (12).

No cells, bioink, living tissues or organs are ever exposed to UV within the device. This is possible due to the gel-forming composition that is exposed to UV containing no cells. Polymerization of the latter in one of the method variation is achieved by UV destruction of liposomes contained in the alginate to release calcium ions. Notably, the UV module radiation is mostly directed in parallel to the printing platform to prevent exposure of the latter to direct radiation, while the diffuse UV radiation is absorbed by the protection module (7).

Figure 6:
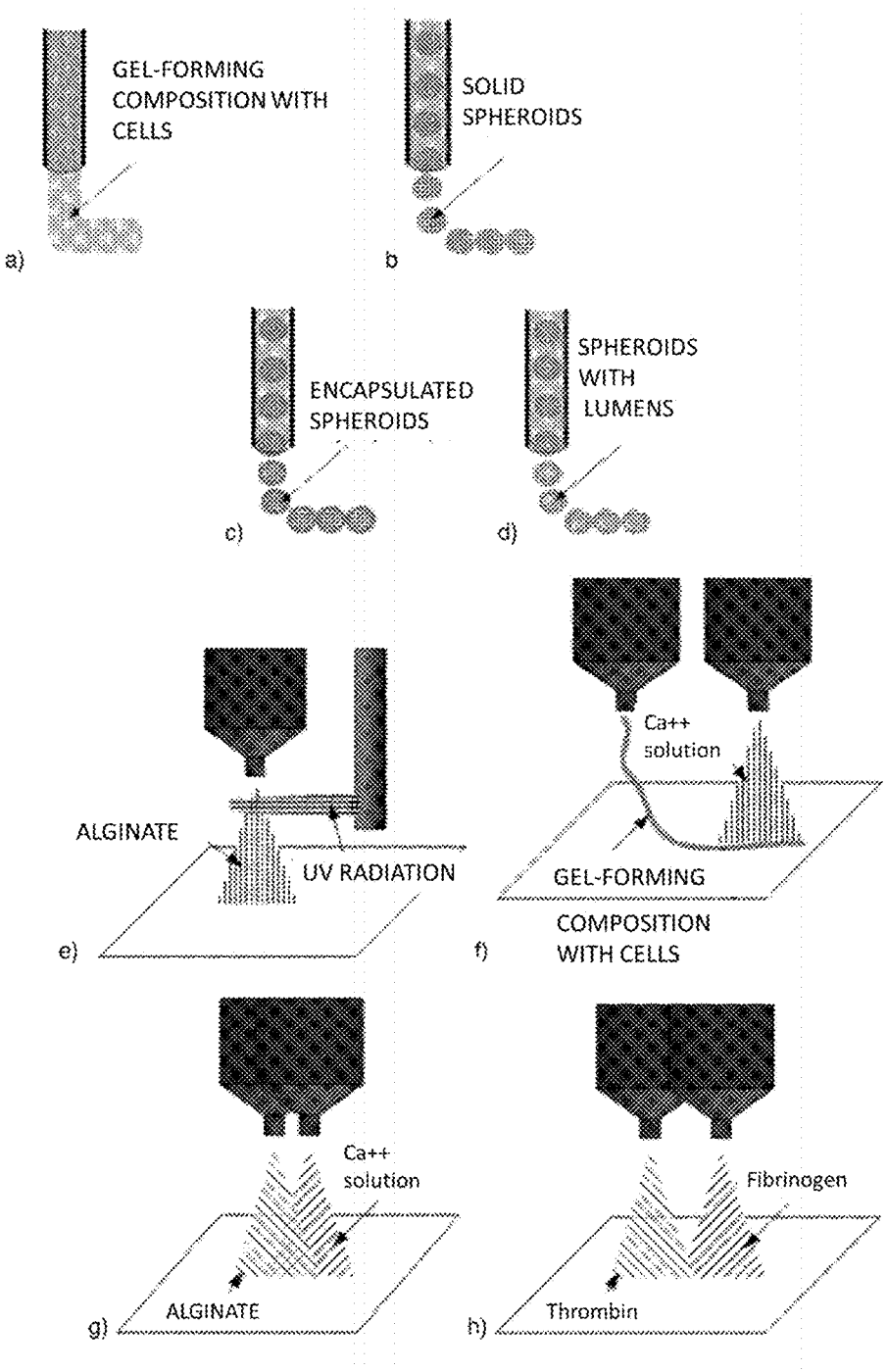
FIG. 6 shows the bioink printing and gel-forming composition application options.
Figure 7:
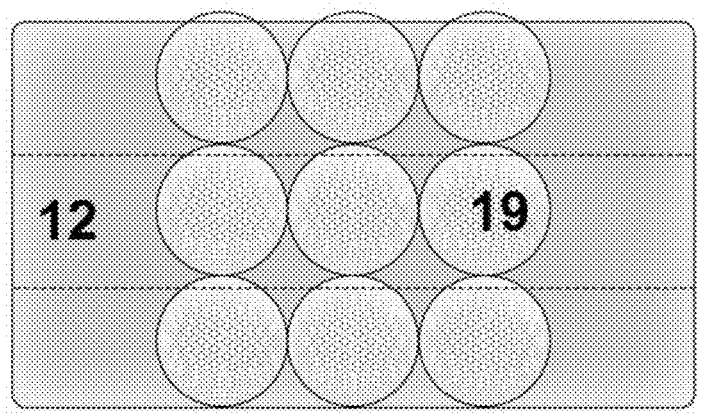
FIG. 7 shows 3 printed layers of hydrogen with spheroids.

Available printing modes include individual and combined modes shown in FIG. 6,7: printing with gel-forming composition containing cells (FIG. 6a), tissue spheroids printing (FIG. 6b), encapsulated spheroids printing (FIG. 6c), spheroids with lumens printing (FIG. 6d), alginate printing with UV (FIG. 6e), alginate with calcium chloride printing (FIG. 6f), alginate with liposomes containing bound calcium (FIG. 6g), thrombin and fibrinogen printing (FIG. 6h).

The examples below show various combined printing modes.

The list of modes includes, but is not limited to, the following modes:

1. alginate polymerization by UV radiation at 365 nm wave length (FIG. 6d) with living-cell hydrogel injected into the polymerized alginate (FIG. 6a);
2. same as 1, but tissue spheroids are injected into polymerized alginate (FIG. 6b).
3. same as 1, but encapsulated spheroids are injected into polymerized alginate (FIG. 6c).
4. same as 1, but spheroids with lumens are injected into polymerized alginate (FIG. 6d).
5. calcium chloride induced alginate polymerization (FIG. 6e) with living-cell hydrogel injected into the polymerized alginate (FIG. 6a);
6. same as 5, but tissue spheroids are injected into polymerized alginate (FIG. 6b).
7. same as 5, but encapsulated spheroids are injected into polymerized alginate (FIG. 6c).
8. same as 5, but spheroids with lumens are injected into polymerized alginate (FIG. 6d).
9. alginate polymerization is induced by UV radiation, which destroys liposomes with calcium, followed by the liberation of calcium ions (FIG. 6g), and then hydrogel containing cells is injected into polymerized alginate (FIG. 6a);
10. same as 9, but tissue spheroids are injected into polymerized alginate (FIG. 6b);
11. same as 9, but encapsulated spheroids are injected into polymerized alginate (FIG. 6c);
12. same as 9, but spheroids with lumens are injected into polymerized alginate (FIG. 6d);
13. thrombin and fibrinogen are used as hydrogels (FIG. 6h), with living-cell hydrogel injected into them (FIG. 6a);
14. same as 13, but tissue spheroids are injected into fibrinogen and thrombin (FIG. 6b);
15. same as 13, but encapsulated spheroids are injected into fibrinogen and thrombin (FIG. 6c);
16. same as 13, but spheroids with lumens are injected into fibrinogen and thrombin (FIG. 6d).

The above description allows a person skilled in the art to easily discern the generic aspects of the invention and perform modifications to adapt it to various tasks and conditions within the character and scope of the invention. Therefore the scope of this invention includes various embodiments.

The invention claimed is:

1. A layer by layer method of biological tissue and organ printing using bioink or a gel-forming composition polymerizing when exposed to UV light, and including the following stages for each individual layer formation:
   a. acquiring data on the object's layer selected for printing;
   b. depositing on the final surface a gel-forming composition polymerizing when exposed to UV light and which in the process of the deposition, after being released from the nozzle and before deposition of the biological tissue or organ being printed, is exposed to UV radiation;
   wherein a bioink printing module is separated from a gel-forming-composition printing module so as to prevent UV radiation from reaching the bioink printing module, the radiation from the UV module being directed predominantly parallel to the platform for printing, so as to prevent UV radiation from reaching the biological tissues and/or organs being printed, and wherein the amount of gel-forming composition is calculated so as to form the required hydrogel layer upon completion of the polymerization;
   c. applying bioink on the layer formed with the gel-forming composition in (b) in accordance with the data acquired in (a); and
   d. waiting on hydrogel polymerization completion,
   wherein spheroids are used as bioink, and
   wherein the ratio between the spheroid diameter and the thickness of the polymerized hydrogel layer is selected so that the thickness of the latter is less than the spheroid diameter.

2. The method of claim 1, wherein the spheroid diameter is between 100 µm and 2.108 mm, and the polymerized hydrogel layer thickness is between 80 µm and 0.6414 mm.

3. The method of claim 1, wherein at least one layer is printed using live-cell hydrogel as bioink.

4. The method of claim 1, wherein polymerization completion time is 5 s to 5 min.

5. The method of claim 1, wherein the gel-forming composition comprises a controlled alginate gel-forming system containing liposomes with bound calcium ions, released from the liposome matrix upon exposure to UV light.

6. The method of any of claims 1-5, wherein at least one layer is printed using bioink and at least two substances capable of polymerization when contacting each other.

7. The method of claim 6, wherein fibrinogen and thrombin are used as the substances capable of polymerization upon contact with each other.

8. The method of claim 6, wherein alginate and calcium ions are used as the substances polymerizing upon getting in contact with each other.

* * * * *